(12) United States Patent
Kim

(10) Patent No.: US 9,329,144 B2
(45) Date of Patent: May 3, 2016

(54) APPARATUS AND METHOD FOR DETECTING BACKLASH AND SLIP

(71) Applicant: Korea Institute of Science and Technology, Seoul (KR)

(72) Inventor: Man-Ho Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/420,160

(22) PCT Filed: Aug. 7, 2013

(86) PCT No.: PCT/KR2013/007115
§ 371 (c)(1),
(2) Date: Feb. 6, 2015

(87) PCT Pub. No.: WO2014/025201
PCT Pub. Date: Feb. 13, 2014

(65) Prior Publication Data
US 2015/0204804 A1    Jul. 23, 2015

(30) Foreign Application Priority Data

Aug. 7, 2012  (KR) .......................... 10-2012-0086164

(51) Int. Cl.
*G01D 5/48* (2006.01)
*G01N 23/207* (2006.01)

(52) U.S. Cl.
CPC .............. *G01N 23/2073* (2013.01); *G01D 5/48* (2013.01); *G01N 2223/331* (2013.01)

(58) Field of Classification Search
CPC ............................ G01N 23/2073; G01D 5/48
See application file for complete search history.

(56) References Cited

U.S. PATENT DOCUMENTS 3,345,613 A * 10/1967 Bucholtz .............. G01N 23/207
341/142

FOREIGN PATENT DOCUMENTS

EP        1 058 105 A1    12/2000
EP        1 411 371 A1     4/2004
(Continued)

OTHER PUBLICATIONS

International Search Report issued on Nov. 5, 2013, in counterpart International Application No. PCT/KR2013/007115 (3 pages, in English).

(Continued)

*Primary Examiner* — David Porta
*Assistant Examiner* — Faye Boosalis
(74) *Attorney, Agent, or Firm* — NSIP Law

(57) ABSTRACT

The detecting apparatus comprises: a monochromator, for Bragg-diffracting the incident beam; an analyzer, on which the beam diffracted by the monochromator is incident, an analyzer Bragg-diffracting the incident beam; a controller, for controlling the driver connected to the monochromator and the analyzer, so as to rotate the analyzer or the monochromator in a first direction and in a second direction opposite to the first direction; and a detector, for detecting the beam diffracted by the analyzer or transmitted through the analyzer while the analyzer or the monochromator is rotating and measuring a backlash and/or a slip of the driver by using the detected beam. The backlash detecting apparatus can measure a backlash and/or a slip in the unit of sub-arcsecond or sub-nanometer by using the radiation beam such as a neutron beam, an X-ray beam or the like.

17 Claims, 2 Drawing Sheets

(56) References Cited

FOREIGN PATENT DOCUMENTS

| | | |
|---|---|---|
| JP | 2000-258366 A | 9/2000 |
| JP | 2000-266567 A | 9/2000 |
| JP | 2001-221752 A | 8/2001 |
| KR | 10-2006-0002591 A | 1/2006 |
| KR | 10-2010-005330 A | 1/2010 |
| KR | 10-2012-0021874 A | 3/2012 |
| WO | WO 2011/161358 A1 | 12/2011 |

OTHER PUBLICATIONS

N. Sarkar, et al., "Backlash Detection in Geared Mechanisms: Modeling, Simulation, and Experimentation," Mechanical Systems and Signal Processing, May 3, 1997, pp. 391-408.

M. Agamalian, et al., "Optimization of a Bonse-Hart Ultra-Small-Angle Neutron Scattering Facility by Elimination of the Rocking-Curve Wings," Journal of Applied Crystallography, vol. 30, Jun. 1997, pp. 345-352.

E. Lee, et al., "A Comprehensive Method of Calibration of Volumetric Positioning Accuracy of CNC-Machines," The International Journal of Advanced Manufacturing Technology, 1998, vol. 14, pp. 43-49.

MP63E User Manual, "M-036 Precision Rotation Stage," Release 3.4.1, Dec. 12, 2004, pp. 4-84, 4-85.

H. Liu, et al., "Backlash Error Measurement and Compensation on the Vertical Machining Center," Engineering, vol. 2, No. 6, Jun. 2010, pp. 4003-407.

Extended European Search Report issued on Jul. 25, 2013, in European Application No. 13152847.3 (10 pages, in English).

* cited by examiner

APPARATUS AND METHOD FOR DETECTING BACKLASH AND SLIP

CROSS-REFERENCE TO RELATED APPLICATIONS

This application is a National Stage of International Application No. PCT/KR2013/007115, filed Aug. 7, 2013 and published as WO 2014/025201 on Feb. 13, 2014, which claims the benefit of Korean Patent Application No. 10-2012-0086164, filed on Aug. 7, 2012, in the Korean Intellectual Property Office, the entire disclosures of which are incorporated herein by reference for all purposes.

TECHNICAL FIELD

The present disclosure relates to an apparatus and method for detecting a backlash and/or a slip, and more particularly, to an apparatus and method which may detect a backlash and/or a slip in the unit of sub-arcsecond or sub-nanometer by using the radiation beam such as a neutron or an X-ray.

BACKGROUND ART

Systems mechanically driven mostly include gears or similar mechanical parts and an electric/electronic-driven device for driving them. Generally, if a pair of gears engage with each other, a gap with a certain space is required between their teeth where a driving gear (a gear generating a primary motion) and a driven gear (a gear generating a secondary motion according to the primary motion) engage with each other. The gap is used for introducing a lubricant between the gear teeth to reduce friction when both gears contact each other or for giving a space for absorbing thermal expansion caused by the material of the teeth.

If the pair of gears engaging with each other moves only in one direction, the gap does not cause a serious problem. However, if the gear pair moves in the opposite direction, the contact between the gear teeth may release so that the gears are instantly detached from each other and do not transfer power, thereby causing an error. Herein, the degree for a driven body, which has been moved to a certain location, to return to an original location is called a backlash.

In a mechanically driven system, the backlash is an important factor for enhancing accuracy of the driving. For example, a rotating plate is a combination of a gear, a linear actuator and an encoder or other combinations similar thereto, and mechanical errors of all, or a part of them influence the degree of the backlash. In addition, the backlash may be influenced by the performance of a motor; precision of gear processing; precision, temperature, humidity, abrasion or the like of a tool used for the gear processing; or the like. For example, in addition to the predictable error as described above, the backlash may accompany a processing error caused by gear fabrication due to a physical or technical limit, which is unpredictable. Even if the processing error is eliminated, the backlash could also be influenced by abrasion caused by long-time use, irregular thermal expansion caused by frictional feat, temperature changes, humidity, or the like.

Therefore, in order to enhance positional prediction in the gear system driven by a motor or the like, it is required to detect a backlash in an accurate and reproducible way. In particular, in industrial fields such as automated systems, precision control, robotics or the like, in which a high degree of precision is demanded, it is necessary to minimize even a small error in the driving system. This makes it important to detect a backlash precisely. In addition, in the technical fields demanding precise repeated works require a driving system to return to a starting position with reproducibility. Although backlash detecting techniques using torque, rotation angle or laser interferometer have been reported, at present the most precise backlash detection resolution is just in the unit of minute.

DISCLOSURE

Technical Problem

Embodiments may provide an apparatus and method for detecting a backlash and/or a slip, which can detect the backlash and/or the slip of a driver with high precision and accuracy in industrial fields demanding high precision such as automated systems, precision control and robotics.

Technical Solution

According to an embodiment, the detecting apparatus includes: a monochromator for Bragg-diffracting the incident beam; an analyzer on which the beam diffracted by the monochromator is incident, the analyzer Bragg-diffracting the incident beam; a controller for controlling the driver connected to the analyzer or the monochromator so as to rotate the analyzer or the monochromator in a first direction and in a second direction opposite to the first direction; and a detector for detecting the beam diffracted by the analyzer or transmitted through the analyzer while the analyzer or the monochromator is rotated and measuring a backlash and/or a slip of the driver from the detected beam.

According to another embodiment, the detecting method includes: Bragg-diffracting a beam by a monochromator; inputting the beam, diffracted by the monochromator, to an analyzer; Bragg-diffracting the beam by the analyzer; rotating the analyzer or the monochromator in a first direction and in a second direction opposite to the first direction by controlling a driver connected to the analyzer or the monochromator; and measuring a backlash and/or a slip of the driver by detecting the beam diffracted by the analyzer or transmitted through the analyzer while the analyzer or the monochromator is rotated.

Advantageous Effects

By using the apparatus and method according to embodiments, it is possible to quantitatively measure the degree of position control of a driving system influencing the production of products in a precision control field where works such as position control, speed control, torque control, step control or the like are repeated. The apparatus and method for detecting a backlash allow detecting a backlash and/or a slip in the unit of sub-arcsecond or sub-nanometer, and can also detect a backlash and/or a slip of a mechanically driving system and its individual driving units. As a result, embodiments may contribute to the development of the precision control fields such as mechanical tools, gears, motors, and electronics, and may also contribute to the development of process conditions such as a driving speed or a minimal step and a minimal transfer region causing idle.

DESCRIPTION OF DRAWINGS

The above and other aspects, features and advantages of the disclosed exemplary embodiments will be more apparent from the following detailed description taken in conjunction with the accompanying drawings in which.

MODE FOR INVENTION

Hereinafter, embodiments of the present disclosure will be described in detail with reference to the drawings.

Figure 1:
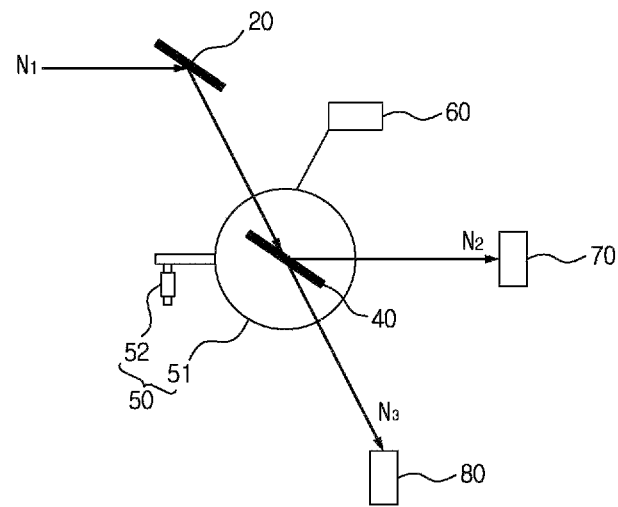
FIG. 1 is a schematic view showing a backlash detecting apparatus capable of measuring a backlash in a diffraction mode or in a transmission mode according to an embodiment.

FIG. 1 is a schematic view showing a backlash detecting apparatus capable of measuring a backlash in a diffraction mode or in a transmission mode according to an embodiment.

Referring to FIG. 1, the backlash detecting apparatus of this embodiment may include a monochromator (20), an analyzer (40), and a controller (60) for controlling a driver (50) to rotate the monochromator (20) or the analyzer (40). In the case the backlash detecting apparatus operates in a diffraction mode, the backlash detecting apparatus may further include a detector (70). Further, in the case the backlash detecting apparatus operates in a transmission mode, the backlash detecting apparatus may further include a detector (80).

In an embodiment, the backlash detecting apparatus may further include a pre-monochromator (not shown). The pre-monochromator may be a single crystal member made of material causing Bragg diffraction, such as anisotropic graphite, silicon, germanium (Ge), calcium chloride (NaCl), lithium fluoride (LiF), calcium carbonate (CaCO$_3$), lead (Pb), copper (Cu), diamond, quartz, gallium arsenide (GaAs), sapphire (Al$_2$O$_3$), beryllium (Be) or other suitable materials. The pre-monochromator is located on a beam path and may selectively induce a specific wavelength component from the beam propagating through the beam path to the monochromator (20) to be focused thereon. For example, the pre-monochromator may Bragg-diffract a neutron beam Ni on the beam path toward the monochromator (20). In an embodiment, the beam used for measuring a backlash may be a neutron beam or an X-ray. Embodiments in the present disclosure will be described based on the neutron beam, but the beam may be used in the embodiments is not limited thereto.

In an embodiment, the neutron beam diffracted by the pre-monochromator may be input to the monochromator (20) through a super mirror guide tube (not shown). The super minor guide tube is a passage of Bragg-reflected neutrons, and a neutron beam incident with an angle smaller than a critical angle is totally reflected by the surface of the super mirror guide tube to prevent a loss of flux. The neutron beam may be focused from the pre-monochromator to the monochromator (20) with a pre-monochromator focusing system.

The monochromator (20) is a single crystal member made of material causing Bragg diffraction, such as highly oriented pyrolitic graphite (HOPG), silicon, germanium (Ge), calcium chloride (NaCl), lithium fluoride (LiF), calcium carbonate (CaCO$_3$), lead (Pb), copper (Cu), diamond, quartz, gallium arsenide (GaAs), sapphire (Al$_2$O$_3$), beryllium (Be) or other suitable materials. The monochromator (20) is placed to have a predetermined direction with respect to the super mirror guide tube (i.e, Bragg angle direction from the pre-monochromator), and a portion of neutrons incident to the monochromator (20) is Bragg-diffracted while another portion of them is transmitted through the monochromator (20). The neutron beam diffracted by the single crystal of the monochromator (20) has a peak when a d-spacing between adjacent planes in the crystal lattice, a wavelength of beam and an incident angle satisfy the Bragg's law. The monochromator (20) is placed to be rotatable within an angular range including a specific angle at which beam is incident at an incident angle satisfying the Bragg's law. In an embodiment, the monochromator (20) may be a Bonse-Hart-Agamalian (BHA) monochromator, without being limited thereto.

The analyzer (40) is placed to be spaced apart from the monochromator (20) and to face the monochromator (20). The neutron beam diffracted by the monochromator (20) is incident on the analyzer (40). Similar to the monochromator (20), the analyzer (40) is a single crystal member made of material causing Bragg diffraction, such as highly oriented pyrolitic graphite (HOPG), silicon, germanium (Ge), calcium chloride (NaCl), lithium fluoride (LiF), calcium carbonate (CaCO$_3$), lead (Pb), copper (Cu), diamond, quartz, gallium arsenide (GaAs), sapphire (Al$_2$O$_3$), beryllium (Be) or other suitable materials. When the analyzer (40) is aligned with the monochromator (20) and placed to be symmetrical thereto, namely in the case the analyzer (40) is arranged so that the neutron beam diffracted with a Bragg angle at the monochromator (20) is incident to the analyzer (40) with the same angle, the neutron beam incident to the analyzer (40) is Bragg-diffracted again at the analyzer (40). The analyzer (40) may be disposed to be rotatable within an angle range including an angle at which the analyzer 40 is aligned with the monochromator 20 and disposed to be symmetrical thereto. In an embodiment, the analyzer (40) may be a Bonse-Hart-Agamalian (BHA) analyzer, without being limited thereto.

In an embodiment, a beam path where the neutron beam passage may be maintained under vacuum or atmospheric pressure. For example, the monochromator (20) and the analyzer (40) may both be placed in one vacuum chamber (not shown), or the monochromator (20) and the analyzer (40) may be placed in different vacuum chambers which are connected to each other by a vacuum pump. For example, the pressure in the chambers where the monochromator (20) and the analyzer (40) are respectively located may be maintained in the range of about $10^{-3}$ torr to about $10^{-2}$ torr, without being limited thereto. A higher-degree vacuum may also be available, if necessary, The monochromator (20) and the analyzer (40) may respectively have a plurality of walls, and a concave-channel structure may be provided between the plurality of walls to form a passage of neutron beam. Alternatively, the monochromator 20 and/or the analyzer (40) may also have a single wall. While embodiments in the present disclosure describe an example where the monochromator and the analyzer have a concave-channel shape with a plurality of reflection surfaces, the configuration of the monochromator and the analyzer are not limited thereto.

Figure 2:
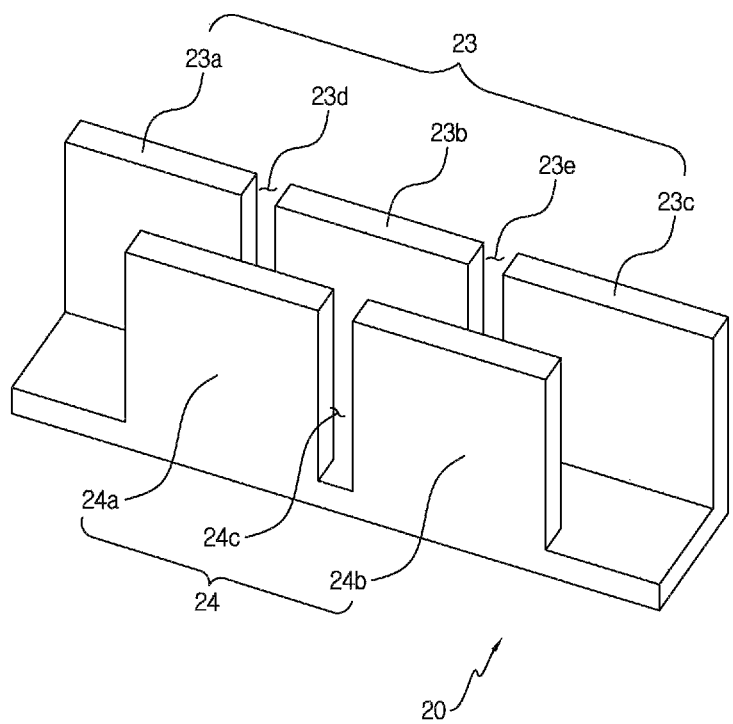
FIG. 2 is a perspective view showing single crystal members of a monochromator and an analyzer employed in the backlash detecting apparatus according to an embodiment.

For example, FIG. 2 is a perspective view showing a single crystal member of the monochromator (20) in the backlash and/or the slip detecting apparatus according to an embodiment.

Referring to FIG. 2, the monochromator (20) may include a first wall (23) and a second wall (24), and a concave-channel structure with a passage of the neutron beam may be provided between the walls. The first wall (23) may have first and second slits (23d), (23e) formed therein so that the first wall (23) may be partitioned into first to third segments (23a), (23b), (23c). A third slit (24c) may be formed in the middle of the second wall (24) so that the second wall (24) is partitioned into fourth and fifth segments (24a), (24b). A shielding body may fill the first to third slits (23d, 23e, 24c) so that a neutron beam does not transmit through each segment. The shielding body may be made of neutron shielding material such as cadmium or gadolinium. The neutron beam progresses as being sequentially reflected on the first segment (23a), the fourth segment (24a), the second segment (23b), the fifth segment (24b) and the third segment (23c). Therefore, while the neutron beam passes through the monochromator (20), five reflections occur. As the number of reflections of the neutron beam is greater, the width of a rocking curve detected by the detector (70) (FIG. 1) decreases. Therefore, reflecting neutrons on the single crystal member of the monochromator (20) several times is advantageous for noise reduction.

FIG. 2 shows a structure of the monochromator (20) where a neutron beam is reflected five times in the first and second walls (23, 24) of the monochromator (20). However, this is just an example, and the monochromator (20) may be designed to reflect a neutron beam 6 or more times or reflecting a neuron beam 4 or less times, without being limited to a design having a specific number of walls or segments.

In addition, FIG. 2 exemplarily illustrates the configuration of a single crystal member used in the monochromator (20) of the backlash and the slip detecting apparatus according to the embodiment of the present disclosure. However, it would be understood by experts in the science and engineering area that the single crystal member may be identically applied not only to the monochromator (20) but also to the analyzer (40).

Referring back to FIG. 1, in an embodiment when the backlash and the slip detecting apparatus operates in a diffraction mode, the backlash and the slip detecting apparatus may include the detector (70). The detector (70) may detect a neutron beam diffracted by the analyzer (40). The neutron beam detected by the detector (70) has a peak when the monochromator (20) and the analyzer (40) are symmetrically placed, namely when the neutron beam diffracted with a predetermined Bragg angle by the monochromator (20) is incident to the analyzer (40) with the same angle. The detector (70) can measure a rocking curve of the detected beam and a peak position of the rocking curve.

In an embodiment, the detector (70) may be a neutron counter for measuring the number of Bragg scattered neutrons. For example, the detector (70) may include an aluminum cylinder filled with helium (III) gas. If neutrons are passed through the aluminum cylinder, the neutrons react with the helium (III) gas, causing resulting in the helium (III) gas being converted into tritium and protons and energy of 764 KeV. The detector (70) measures the number of neutrons by amplifying the generated energy to a high voltage. However, it is just an example, and the detector (70) might also have other configurations to measure the intensity of a neutron beam by using other detection principles.

The controller (60) may rotate one of the monochromator (20) and the analyzer (40) by controlling the rotation driving means connected to the monochromator (20) or the analyzer (40). Hereinafter, the case where the controller (60) controls the driver (50) connected to the analyzer 40 to rotate the analyzer 40 is described. However, it would be easily understood by the experts that the principle of the present disclosure may be identically applied to another case where the monochromator (20) is rotated instead of the analyzer (40).

The driver (50) may include a rotation driving means for rotating the analyzer (40). For example, the driver (50) includes a rotating plate (51) and a spinel (52). The analyzer (40) may be placed on the rotating plate (51), so that the rotating plate (51) and the analyzer (40) on the rotating plate (51) may rotate in both directions by moving a tip of the spinel (52) in forward and reverse directions. However, it is just an example, and in another embodiment, the driver (50) may have another kind of rotation driving means such as a motor which may rotate the analyzer (40) in both directions.

The controller (60) may rotate the analyzer (40) in both directions within an angle range including a predetermined angle (as used herein, "first angle") in which the beam Bragg-diffracted by the monochromator (20) is Bragg-diffracted again by the analyzer (40) since the monochromator (20) and the analyzer (40) are aligned symmetrically. For example, the controller (60) may rotate the analyzer (40) in a positive direction from a second angle smaller than the first angle to a third angle greater than the first angle, and then reversely rotate the analyzer (40) in an opposite direction (i.e., in a negative direction) from the third angle to the second angle. However, the rotation angles of the analyzer (40) in both directions may not be identical to each other, and the analyzer (40) may be rotated in a certain range such that the first angle where a peak is to be detected is passed through in both directions.

The detector (70) measures a first rocking curve by detecting a neutron beam $N_2$ diffracted by the analyzer 40 while the analyzer (40) is rotating from the second angle to the third angle. Further, the detector (70) measures a second rocking curve by detecting a neutron beam $N_2$ diffracted by the analyzer (40) while the analyzer (40) is reversely rotating in an opposite direction, namely in the negative direction, from the third angle to the second angle. The detector (70) measures a backlash of the driver (50) rotating the analyzer (40), by comparing a peak position of the first rocking curve and a peak position of the second rocking curve.

For example, after setting the first angle to be 0°, a rocking curve is measured by rotating the analyzer (40) from an initial negative angle through 0° to a positive angle, and a peak position Pf1 of the rocking curve is measured. If the analyzer (40) reaches a predetermined positive angle or above, a rocking curve is measured again by rotating the analyzer (40) in the reverse direction through 0° to the initial negative angle, and a peak position Pr2 of the rocking curve is measured. The difference between Pr2 and Pf1 (i.e., Pr2 ?Pf1) is defined as an reverse direction backlash of the driver (50).

Meanwhile, in an embodiment, a rocking curve can be measured while rotating the analyzer (40), which has rotated to the starting position in the reverse direction, in the positive direction again, and a peak position Pr1 and Pf2 of the rocking curve can be measured. At this time, the difference between Pr1 and Pf2 (namely, Pf2 ?Pr1) can be defined as a positive direction backlash.

Figure 3:
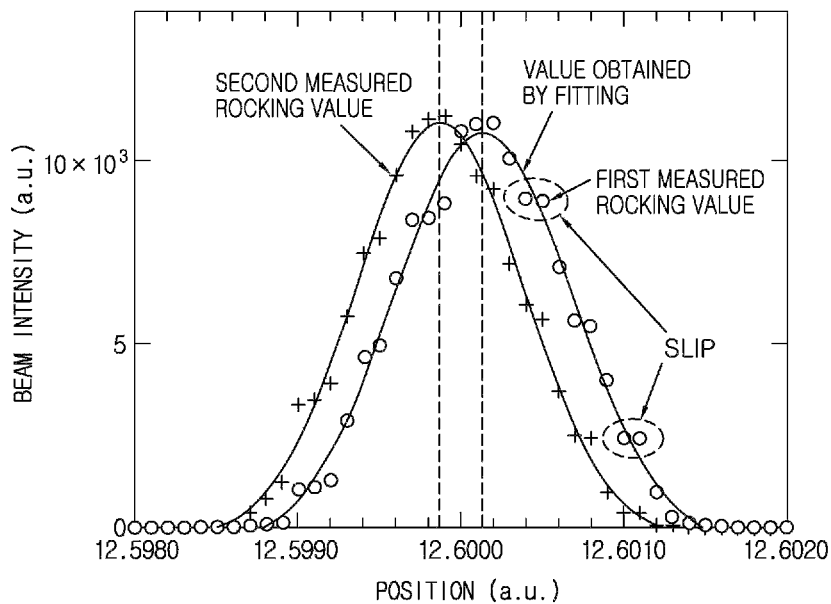
FIG. 3 is a graph showing an example of a backlash and a slip of a driver, measured in a diffraction mode by using the backlash detecting apparatus according to the embodiment.

FIG. 3 is a graph showing an example of a backlash of a driver, measured in a diffraction mode by using the backlash detecting apparatus according to the embodiment.

FIG. 3 shows a first rocking curve by using measurement values (symbol O) obtained by measuring the intensity of beam while rotating the analyzer in the positive direction from an initial negative angle to a positive angle. FIG. 3 also shows a second rocking curve by using measurement values (symbol +) obtained by measuring the intensity of beam while returning the analyzer to the initial negative angle. Further, a solid line near each symbols O, + represents a result obtained by fitting each measurement value with a normal distribution function (Gaussian function). As shown in FIG. 3, the peak position of the first rocking curve is different from the peak position of the second rocking curve, which means that, when rotating the analyzer in the positive direction and then returning the analyzer to the original location in the reverse direction, the driver rotating the analyzer does not completely return to the original location. By comparing the peak position of the first rocking curve with the peak position of the second rocking curve, the backlash of the rotation driver can be measured.

When measuring a backlash, the measured rocking curve may be used without modification. However, if necessary, as shown with the solid lines in FIGS. 3 and 4, a more accurate peak position may also be obtained by fitting a certain region by using a normal distribution function to the rocking curve or the like. The measured backlash may be a linear movement distance or a rotating angle of an actuator, a spinel gear or the like depending on the rotation driver, and the linear distance and the rotation angle may be mutually converted. For example, the rotation angle can be obtained by applying arctan to a result obtained by dividing the straight movement distance of the driver by a rotating radius. In the graph depicted in FIG. 3, if the shape of the driver is considered, the backlash is measured as 0.2 mm or 0.4 arcsec.

By using the method described above with reference to FIGS. 1 to 3, the backlash caused by a gap between gear teeth in the driver (50) and/or an actuator and an encoder in the driver (50) may be precisely measured in the unit of sub-arcsecond or sub-nanometer. Meanwhile, the driver (50) may be configured as a combination of a plurality of parts. In this case, the backlash measured by using the method described above is a backlash of the entire driver (50). A backlash of an individual part may be obtained by measuring a backlash while exchanging individual parts of the driver (50) in order.

In addition, by using the operation of the detector (70) described above, a minimal step at which a power transmission system is capable of operating and a minimal displacement required for repetitive behaviors could be measured. There may be a case where power is not easily transmitted to a motor, an actuator, a gear and a rotating plate when a step increment is too small or in a case of returning to the original location after movement as much as a minute angle or a minute distance. The driving controller may send a power transmission signal and recognize that a mechanical system is operating, but in fact, a slip may happen at a gap between gears, which makes the machine run idle. However, when the detector (70) measures a rocking curve according to the embodiments, it is possible to know whether power is transmitted, together with the backlash. In other words, if power is not transmitted, the intensity of neutron beam or X-ray beam detected by the detector (70) does not change.

In addition to the backlash, FIG. 3 shows two angles where the slip has been occurred, each angle having two points from the rocking curve. In order to determine the occurrence of the slip, the detector (70) may detect points from the first and/or second rocking curves. If there are points which correspond to two or more successive angles and have close to or identical intensities, the detector may determine that those points correspond to a slip phenomenon. The slip phenomena can be measured during rocking curve measurement in the diffraction mode.

Meanwhile, even though the backlash of the driver (50) is measured while the controller (60) rotates the analyzer (40) by using the driver (50) in the above embodiments, a backlash may also be measured by using the same principle when the controller rotates the monochromator (20) instead of the analyzer (40). In other words, the backlash detecting apparatus may include a rotation driving means (not shown) such as a rotating plate and a spinel, connected to the monochromator (20). The controller (60) can rotate the monochromator (20) by using the rotation driving means, and may measure a backlash of the rotation driving means of the monochromator (20) by using the change of the peak position of the rocking curve detected by the detector (70) while the monochromator (20) is rotating.

Referring back to FIG. 1, in an embodiment, if the backlash and the slip detecting apparatus operates in a transmission mode, the backlash and the slip detecting apparatus may include the detector (80). In this embodiment, the detector (80) is different from the detector (70) described above with reference to FIG. 1 in that the detector (80) detects a neutron beam $N_3$ transmitted through the analyzer (40), instead of a neutron beam diffracted by the analyzer (40). In other words, the detector (80) has a function of monitoring transmitted neutrons. For this, the detector (80) is placed on an extension line of the beam path of the neutron beam, incident to the analyzer (40), which extends through the analyzer (40). The detecting process of the detector (80) may be easily understood from the operation of the detector (70) described above with reference to FIG. 1. However, in the case the monochromator (20) and the analyzer (40) are symmetrically placed, since the neutron beam Bragg-diffracted at the monochromator (20) is mostly Bragg-diffracted at the analyzer (40) and advances toward the detector (70), the rocking curve detected by the transmission detector (80) has a peak showing a minimum value.

Figure 4:
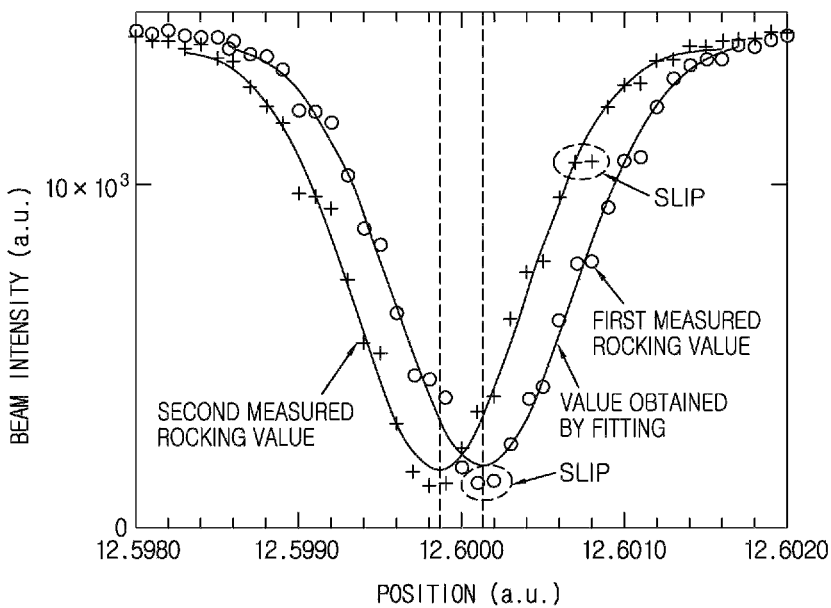
FIG. 4 is a graph showing an example of a backlash and a slip of a driver, measured in a transmission mode by using the backlash detecting apparatus according to the embodiment.

FIG. 4 is a graph showing an example of a backlash of a driver, measured in a transmission mode by using the backlash detecting apparatus according to the embodiment.

FIG. 4 shows a first rocking curve (symbol O) obtained by measuring the intensity of beam while rotating the analyzer in the positive direction from an initial negative angel to a positive angle and also shows a second rocking curve (symbol +) obtained by measuring the intensity of beam while returning the analyzer to the initial negative angle. Further, a solid line near each symbols O, + represents a result obtained by fitting each measured value with a normal distribution function (Gaussian function). As shown in FIG. 4, the peak position of the first rocking curve is different from the peak position of the second rocking curve, and a backlash of the driver rotating the analyzer can be measured therefrom.

In addition to the backlash, FIG. 4 shows two angles where the slip has been occurred, each angle having two points from the rocking curve. If there are points which correspond to two or more successive angles and have close to or identical intensities, those points may correspond to a slip phenomenon. These slip phenomena can be measured during rocking curve measurement in the transmission mode.

Using the apparatus and method according to the embodiments described above, it is possible to quantitatively measure the degree of position control precision of a driving system influencing the production of products in a precision control field where works such as position control, speed control, torque control, step control or the like are repeated. The apparatus and method can detect a backlash and/or a slip in the unit of sub-arcsecond or sub-nanometer, and so may contribute to the development of the precision control fields such as mechanical tools, gears, motors, and electronics.

For example, in the case where a step is designed to be small in order to control precise operations of a motor according to conventional arts, the gear may run idle if the step is too small or a displacement distance is too short. Herein, the apparatus and method for detecting a backlash according to the embodiments may be used to measure a minimal step and a minimal transfer region which cause idle (i.e., slip). Further, since a driving system has a physical limit in its velocity of motion, an error of the driving system may increase when the velocity of motion is too fast or too slow. Herein, the apparatus and method for detecting a backlash according to the embodiments may be used to measure a suitable driving speed.

While the exemplary embodiments have been shown and described, it will be understood by an expert that various changes in form and details may be made thereto without departing from the spirit and scope of the present disclosure as defined by the appended claims. In addition, many modifications can be made to adapt a particular situation or material to findings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

INDUSTRIAL APPLICABILITY

The present disclosure relates to an apparatus and method for detecting a backlash and/or a slip, and more particularly, to an apparatus and method which may detect a backlash and/or a slip in the unit of sub-arcsecond or sub-nanometer by using the radiation beam such as a neutron or an X-ray.

The invention claimed is:

1. A detecting apparatus, comprising:
a monochromator for Bragg-diffracting an incident beam;
an analyzer on which the beam diffracted by the monochromator is incident, the analyzer Bragg-diffracting the incident beam;
a controller for controlling a driver connected to the analyzer or the monochromator so as to rotate the analyzer or the monochromator in a first direction and in a second direction opposite to the first direction; and
a detector for detecting the beam diffracted by the analyzer or transmitted through the analyzer while the analyzer or the monochromator is rotating and measuring a backlash and/or a slip of the driver by using the detected beam,
wherein the detector is configured to measure a first rocking curve by detecting the beam while the analyzer or the monochromator is rotating in the first direction, measure a second rocking curve by detecting the beam while the analyzer or the monochromator is rotating in the second direction, and measure the backlash from a difference between a peak position of the first rocking curve and a peak position of the second rocking curve.

2. The detecting apparatus according to claim 1,
wherein, when a rotation angle of the analyzer or the monochromator is a first angle, the monochromator and the analyzer are aligned and symmetrically disposed,
wherein the controller rotates the analyzer or the monochromator from a second angle to a third angle in the first direction and from the third angle to the second angle in the second direction, and
wherein the first angle is between the second angle and the third angle.

3. The detecting apparatus according to claim 1,
wherein the detector is configured to detect the beam diffracted by the analyzer, and
wherein the peak of the first rocking curve and the peak of the second rocking curve are points where the detected beam has a maximum intensity.

4. The detecting apparatus according to claim 1,
wherein the detector is configured to detect the beam transmitted through the analyzer, and
wherein the peak of the first rocking curve and the peak of the second rocking curve are points where the detected beam has a minimum intensity.

5. The detecting apparatus according to claim 1, wherein the detector is configured to measure the slip based on points from the first and second rocking curves where two or more successive angles have substantially the same intensity to each other.

6. The detecting apparatus according to claim 1,
wherein the monochromator comprises a plurality of segments spaced apart from each other by a slit or a single segment, and wherein the beam is diffracted by each of the plurality of segments or by the single segment.

7. A detecting apparatus, comprising:
a monochromator for Bragg-diffracting an incident beam;
an analyzer on which the beam diffracted by the monochromator is incident, the analyzer Bragg-diffracting the incident beam;
a controller for controlling a driver connected to the analyzer or the monochromator so as to rotate the analyzer or the monochromator in a first direction and in a second direction opposite to the first direction; and
a detector for detecting the beam diffracted by the analyzer or transmitted through the analyzer while the analyzer or the monochromator is rotating and measured a backlash and/or a slip of the driver by using the detected beam,
wherein the controller is configured to rotate the analyzer or the monochromator sequentially in the first direction, in the second direction and in the first direction, and
wherein the detector is configured to measure a first rocking curve and a second rocking curve by detecting the beam while the analyzer or the monochromator rotates in the first direction twice, and measures the backlash from a difference between a peak position of the first rocking curve and a peak position of the second rocking curve.

8. The detecting apparatus according to claim 7,
wherein the detector is configured to detect the beam diffracted by the analyzer, and wherein the peak of the first rocking curve and the peak of the second rocking curve are points where the detected beam has a maximum intensity.

9. The detecting apparatus according to claim 7,
wherein the detector is configured to detect the beam transmitted through the analyzer, and
wherein the peak of the first rocking curve and the peak of the second rocking curve are points where the detected beam has a minimum intensity.

10. A detecting method, comprising:
Bragg-diffracting a beam by a monochromator;
inputting the beam, diffracted by the monochromator, to an analyzer;
Bragg-diffracting the beam by the analyzer;
rotating the analyzer or the monochromator in a first direction and in a second direction opposite to the first direction by controlling a driver connected to the analyzer or the monochromator; and
measuring a backlash and/or a slip of the driver by detecting the beam diffracted by the analyzer or transmitted through the analyzer while the analyzer or the monochromator is rotating,
wherein the measuring of the backlash comprises:
measuring a first rocking curve by detecting the beam while the analyzer or the monochromator is rotating in the first direction, measuring a second rocking curve by detecting the beam while the analyzer or the monochromator is rotating in the second direction, and measuring the backlash from a difference between a peak position of the first rocking curve and a peak position of the second rocking curve.

11. The detecting method according to claim 10, wherein said rotating comprises:

rotating the analyzer or the monochromator from a second angle to a third angle in the first direction; and rotating the analyzer or the monochromator from the third angle to the second angle in the second direction, wherein a first angle where the monochromator and the analyzer are aligned and symmetrically disposed is between the second angle and the third angle.

12. The detecting method according to claim 10, wherein said measuring of the first rocking curve and said measuring of the second rocking curve respectively comprise detecting the beam diffracted by the analyzer, and wherein the peak of the first rocking curve and the peak of the second rocking curve are points where the beam has a maximum intensity.

13. The detecting method according to claim 10, wherein said measuring of the first rocking curve and said measuring of the second rocking curve respectively comprise detecting the beam transmitted through the analyzer, and wherein the peak of the first rocking curve and the peak of the second rocking curve are points where the beam has a minimum intensity.

14. The detecting method according to claim 10, wherein said measuring of the slip comprises:

measuring the slip based on points from the first and second rocking curves where two or more successive angles have substantially the same intensity to each other.

15. A detecting method, comprising:

Bragg-diffracting a beam by a monochromator;

inputting the beam, diffracted by the monochromator, to an analyzer;

Bragg-diffracting the beam by the analyzer;

rotating the analyzer or the monochromator in a first direction and in a second direction opposite to the first direction by controlling a driver connected to the analyzer or the monochromator; and measuring a backlash and/or a slip of the driver by detecting the beam diffracted by the analyzer or transmitted through the analyzer while the analyzer or the monochromator is rotating, wherein said rotating comprises rotating the analyzer or the monochromator sequentially in the first direction, in the second direction and in the first direction, wherein said measuring of the backlash comprises:

measuring a first rocking curve by detecting the beam while the analyzer or the monochromator is first rotating in the first direction;

measuring a second rocking curve by detecting the beam while the analyzer or the monochromator is second rotating in the first direction; and measuring the backlash from a difference between a peak position of the first rocking curve and a peak position of the second rocking curve.

16. The detecting method according to claim 15, wherein said measuring of the first rocking curve and said measuring of the second rocking curve respectively comprise detecting the beam diffracted by the analyzer, and wherein the peak of the first rocking curve and the peak of the second rocking curve are points where the beam has a maximum intensity.

17. The detecting method according to claim 15, wherein said measuring of the first rocking curve and said measuring of the second rocking curve respectively comprise detecting the beam transmitted through the analyzer, and wherein the peak of the first rocking curve and the peak of the second rocking curve are points where the beam has a minimum intensity.

\* \* \* \* \*